US008956411B2

(12) United States Patent
Ingham et al.

(10) Patent No.: US 8,956,411 B2
(45) Date of Patent: Feb. 17, 2015

(54) PREPARATION OF TISSUE FOR MENISCAL IMPLANTATION

(75) Inventors: Eileen Ingham, Leeds (GB); John Fisher, Leeds (GB); Thomas Stapleton, Leeds (GB); Joanne Ingram, Leeds (GB)

(73) Assignee: University of Leeds (GB)

( * ) Notice: Subject to any disclaimer, the term of this patent is extended or adjusted under 35 U.S.C. 154(b) by 1251 days.

(21) Appl. No.: 12/514,703

(22) PCT Filed: Nov. 13, 2007

(86) PCT No.: PCT/GB2007/004349
§ 371 (c)(1),
(2), (4) Date: Dec. 4, 2009

(87) PCT Pub. No.: WO2008/059244
PCT Pub. Date: May 22, 2008

(65) Prior Publication Data
US 2010/0152852 A1 Jun. 17, 2010

(30) Foreign Application Priority Data

Nov. 16, 2006 (GB) .................................. 0622846.4
Apr. 19, 2007 (GB) .................................. 0707555.9

(51) Int. Cl.
*A61F 2/38* (2006.01)
*A61L 27/36* (2006.01)

(52) U.S. Cl.
CPC ........... *A61L 27/3612* (2013.01); *A61F 2/3872* (2013.01); *A61L 27/3683* (2013.01); *A61L 2430/40* (2013.01)
USPC ........................................ 623/14.12; 435/1.3

(58) Field of Classification Search
None
See application file for complete search history.

(56) References Cited

U.S. PATENT DOCUMENTS

| 5,632,778 A | 5/1997 | Goldstein |
| 2002/0119437 A1 | 8/2002 | Grooms et al. |
| 2003/0014126 A1 | 1/2003 | Patel et al. |
| 2004/0067582 A1 * | 4/2004 | Wolfinbarger et al. ....... 435/366 |
| 2005/0013870 A1 * | 1/2005 | Freyman et al. .............. 424/520 |
| 2005/0013872 A1 | 1/2005 | Freyman |

FOREIGN PATENT DOCUMENTS

| JP | 2003180819 A | 7/2003 |
| WO | WO 95/24873 A1 | 9/1995 |
| WO | WO 01/49210 A1 | 7/2001 |
| WO | WO 03/002165 A1 | 1/2003 |
| WO | WO 03/007784 A2 | 1/2003 |
| WO | WO 2004/103461 A1 | 12/2004 |
| WO | WO 2005/063314 A1 | 7/2005 |
| WO | WO 2005/063316 A1 | 7/2005 |
| WO | WO 2005/089411 A2 | 9/2005 |

OTHER PUBLICATIONS

Anderst et al., OsteoArthritis and Cartilage (2005) vol. 13, No. 9, pp. 808-816.*
Arnoczky et al., Arthroscopy: The Journal of Arthroscopic and Related Surgery, vol. 8. No. 4, pp. 428-436, 1992.*
Ferguson et al., The 2006 Meniscus Transplantation Study Group, 2006MTSGProgram, Mar. 23, 2006, pp. 1-14.*
Kaur et al., Journal of Academia and Industrial Research (JAIR), vol. 2, Issue 4, Sep. 2013, pp. 226-229.*
Notification of Transmittal of the International Search Report and the Written Opinion of the International Searching Authority, or the Declaration corresponding to International Application No. PCT/GB2007/004349 mailed May 4, 2009.
Notification Concerning Transmittal of International Preliminary Report on Patentability corresponding to International Application No. PCT/GB2007/004349 mailed May 28, 2009.
Tomizawa "Development of a small-caliber vascular graft with antithrombogeniety by high hydrophilleity", *Jpn. J. Artif. Organs* 17(4):1523-1528 (1988).
Yamasaki et al. "Meniscal regeneration using tissue engineering with a scaffold derived from a rat meniscus and mesenchymal stromal cells derived from rat bone marrow", Wiley Periodicals, Inc. www.interscience.wiley.com) pp. 2-9 (2005).
Office Action corresponding to Japanese Application No. 2009-536787 issued Jan. 29, 2013.

* cited by examiner

*Primary Examiner* — Allison Fox
*Assistant Examiner* — Yvonne Pyla
(74) *Attorney, Agent, or Firm* — Myers Bigel Sibley & Sajovec, P.A.

(57) ABSTRACT

The present invention relates to a method of preparing a tissue matrix and its subsequent use in the replacement and/or repair of a damaged or defective meniscus. The invention also provides meniscal tissue that is substantially decellularised.

27 Claims, 9 Drawing Sheets

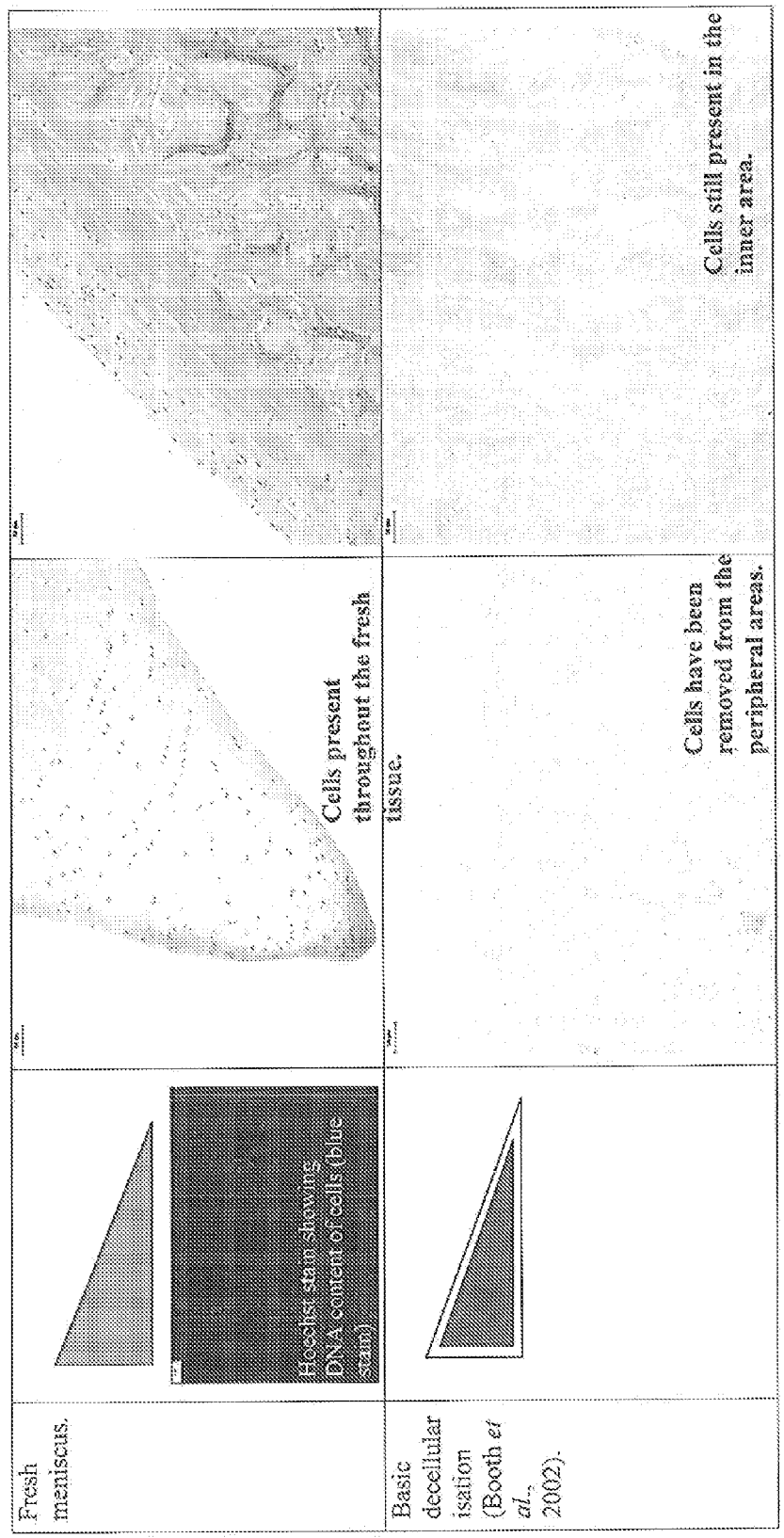

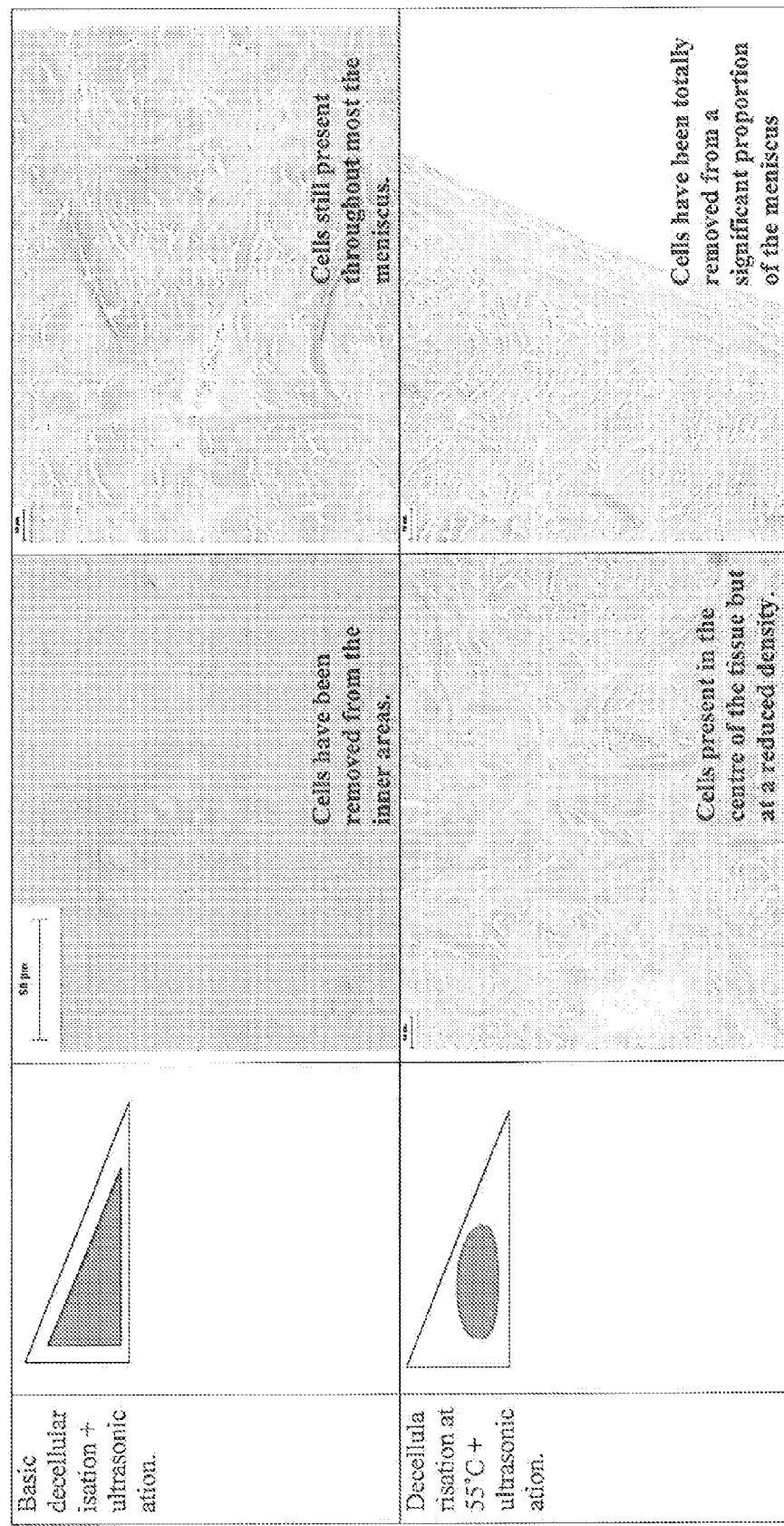

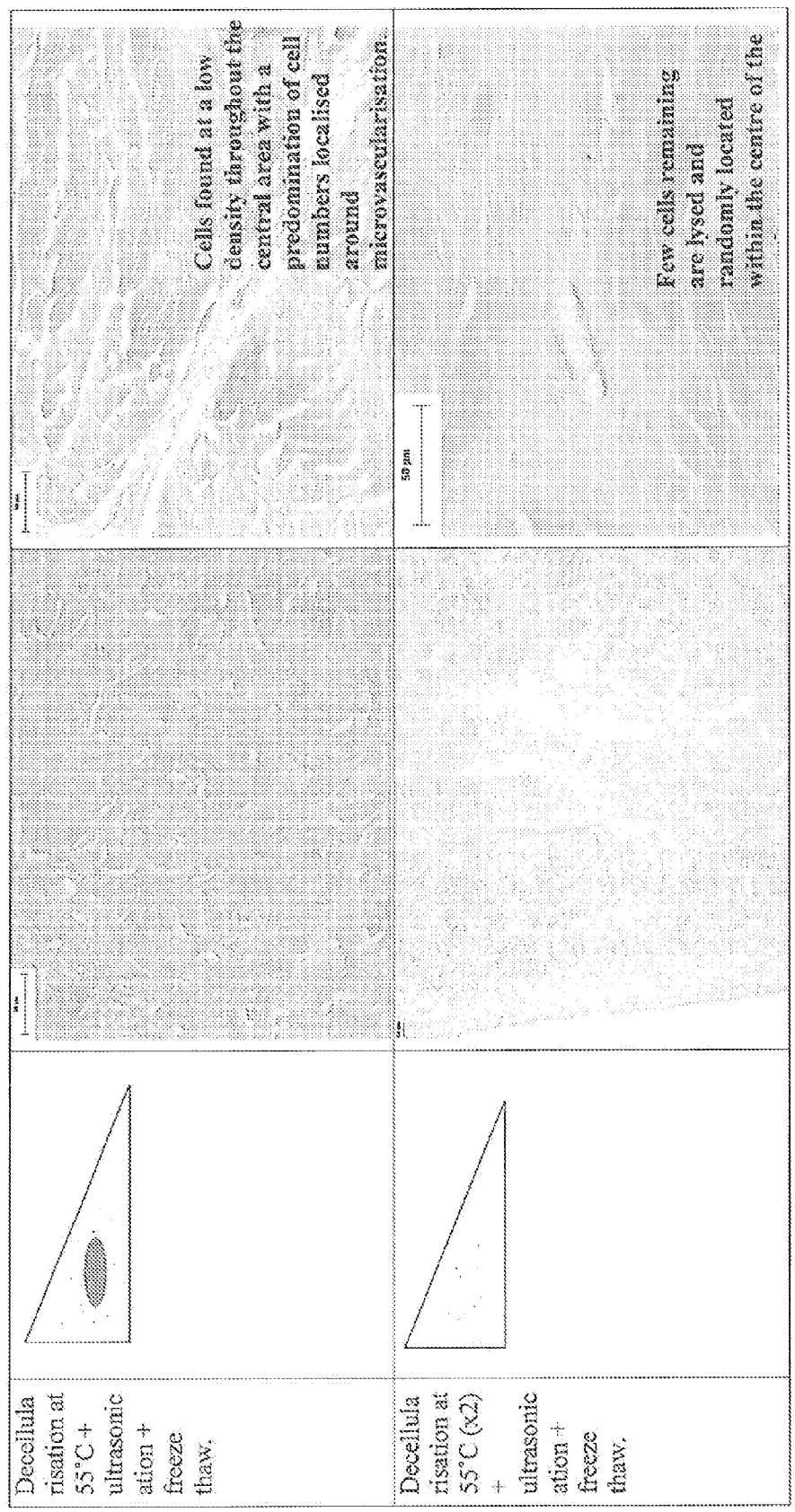

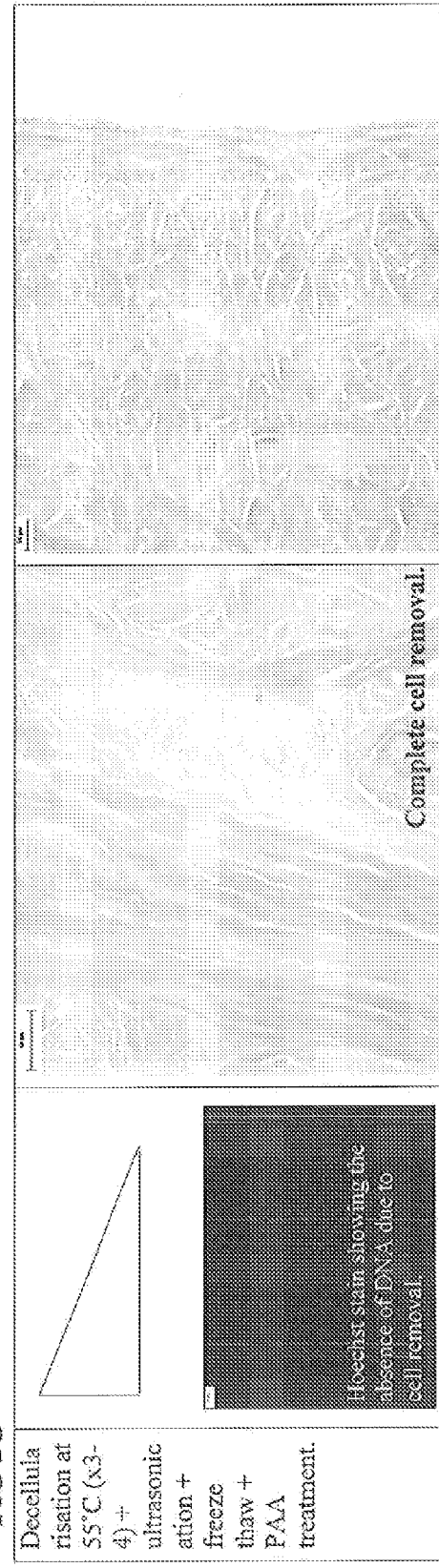

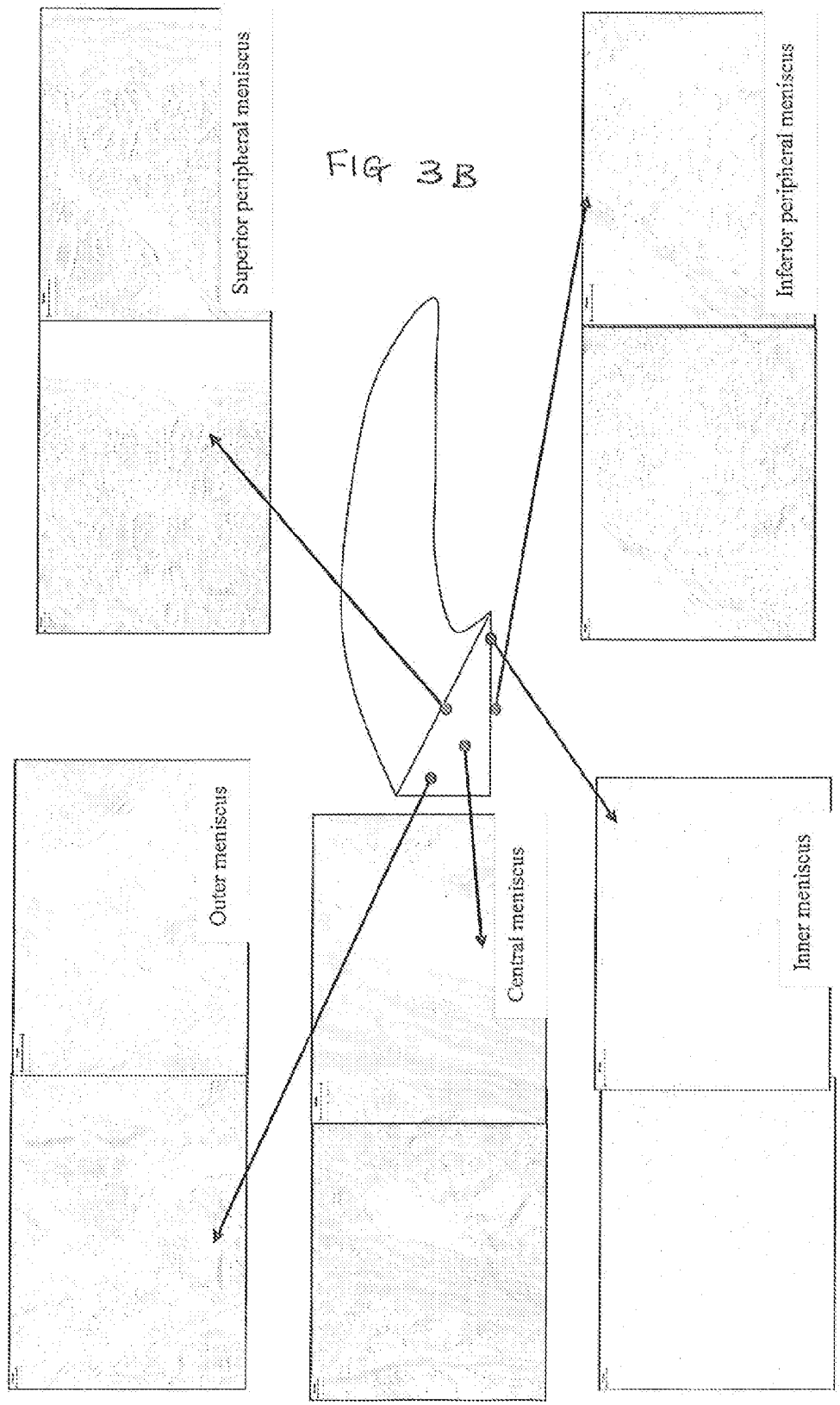

Alpha Gal Fresh

Alpha Gal Decellularised

PREPARATION OF TISSUE FOR MENISCAL IMPLANTATION

RELATED APPLICATIONS

The present application is a 35 U.S.C. §371 national phase application of PCT International Application No. PCT/GB2007/004349, having an international filing date of Nov. 13, 2007, claiming priority to Great Britain Patent Application No. 0622846.4, filed Nov. 16, 2006 and further claiming priority to Great Britain Patent Application No. 0707555.9, filed Apr. 19, 2007. The disclosures of each application are incorporated herein by reference in their entireties. The above PCT International Application was published in the English language as International Publication No. WO 2008/059244A2.

The present invention relates to a method of preparing a tissue matrix, especially a soft tissue matrix, for the replacement and/or repair of a damaged or defective meniscus. The invention also provides a meniscus tissue that is substantially decellularised for subsequent transplantation/implantation.

BACKGROUND

The human knee is an important and complex joint comprising three spatially inter-related bones (the femur, tibia and patella), ligaments and cartilaginous structures all of which interact to create a variety of motions. The surfaces of the knee bones within the joint are covered with articular cartilage. This important surface allows the bones to smoothly glide against each other without causing damage to the bone. The meniscus, a C-shaped cartilage cushion sits between the articular cartilage surfaces of the bone and acts as a shock absorber by distributing weight and so improves the overall stability of the knee joint. Each knee joint has a medial and lateral meniscus which is composed of fibrochondrocytes, proteoglycans and an extra-cellular matrix of collagen and elastin fibres. When menisci are damaged through injury, disease or inflammation arthritic changes can develop in the knee joint with consequent swelling, pain and/or loss of knee joint function in the affected individual. Whilst it is possible to repair a torn meniscus, a meniscus that is severely damaged or has an extensive tear may have to be removed.

Since joint cartilage in adults does not naturally regenerate to a significant degree once it is destroyed, damaged adult menisci have historically been treated by a variety of surgical interventions including removal and replacement with prosthetic devices. In older patients, a knee joint replacement is often the preferred option. However, for younger individuals (those under 50 or 55 years old) the alternative to replacing the entire joint is a meniscal transplant which uses either prosthetic menisci or donor tissue to replace the damaged meniscus.

A problem associated with the use of donor tissue for meniscal replacement is that the meniscus is a dense fibrocartilagenous tissue impregnated throughout with fibrochondrocytes which are the cells responsible for synthesis, maintenance and repair of the extracellular matrix. The human medial meniscus is approximately 4.5 mm in length and the lateral meniscus is approximately 3.5 mm in length, the thickness of each range from 25 to 35 mm (porcine values are similar to those of human menisci.) Because the meniscus is a thick and dense tissue with cells located throughout and especially around the microvasculature it is extremely difficult to decellularise, especially at the central regions, which in turn means that it is difficult to prepare an immunologically inert or decellularised tissue for transplantation and so there is a risk of rejection. In other words there is low biocompatibility and a high risk of the host having an immunological reaction from either a heterograft or xenograft.

In order to provide an acellular biocompatible meniscal implant, artificial meniscal prostheses have been developed. However, a problem associated with an artificial meniscal prosthesis is that it not as robust as natural meniscal tissue and also it is deficient in the elastic properties of the natural menisci consequently such prostheses are not as effective at shock absorption as the natural material.

A method that could effectively decellularise donor meniscal tissue would offer immediate benefit to the treatment of individuals requiring a meniscal implant/transplant.

BRIEF SUMMARY OF THE DISCLOSURE

According to a first aspect of the invention there is provided a method of preparing donor meniscal tissue for subsequent implantation into a host comprising the steps of:
  (i) ultrasonicating the tissue in a buffered solution;
  (ii) freezing and thawing the tissue;
  (iii) incubating the tissue in a hypotonic solution;
  (iv) incubating the tissue in a hypotonic solution comprising an anionic detergent;
  (v) repeating steps (iii) and (iv);
  (vi) incubating the tissue in a solution comprising at least one nuclease enzyme; and
  (vii) washing the tissue with an oxidising agent.

Preferably, step (ii) can be performed in advance of step (i), that is to say that the donor meniscal tissue can be subjected to a freeze/thaw procedure in advance of the ultrasonication procedure, the order of these two steps is not intended to limit the scope of the invention.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

In one embodiment of the invention the method comprises preparing a donor meniscal tissue for subsequent implantation into a host comprising the steps of:
  (i) freezing and thawing the tissue;
  (ii) incubating the tissue in a hypotonic solution;
  (iii) incubating the tissue in a hypotonic solution comprising an anionic detergent;
  (iv) repeating steps (ii) and (iii);
  (v) incubating the tissue in a solution comprising at least one nuclease enzyme; and
  (v) washing the tissue with an oxidising agent.

In this embodiment of the invention the step of ultrasonicating the tissue in a buffered solution is omitted. It has been found that the method of the present invention may be successfully accomplished without the step of ultrasonication however, it is believed that such a step allows for improved recellularisation on implantation once the meniscal tissue is decellularised. It is therefore an optional and preferred step in the invention but one that may be required to improve subsequent recellularisation and therefore in some instance will be performed as part of the method of the present invention.

It will be appreciated that the meniscus is obtainable by removing the whole or a portion of a medial or lateral meniscus from a knee joint of an allogeneic or xenogeneic donor Preferably the recipient of the prepared meniscus is a human, alternatively the recipient may be any other species that requires a meniscal implant as a result of damage or degeneration of said tissue.

A xenograft or xeno-transplant is a transplant of tissue from a donor of one species to a recipient of another species. The terms heterograft and hetero-transplant are also sometimes used, while the term homograft or allograft refers to a same-species transplant.

In the present invention, where the recipient is a human, the donor is preferably a human or any other mammal that has a meniscus of approximately commensurate physiological properties such as thickness and strength.

Preferably the meniscal donor tissue is either human or porcine in origin.

As herein before stated decellularisation may be achieved in the absence of ultrasonication however when included in the method of the present invention, the ultrasonication step is carried out in phosphate buffered saline (PBS) or any other physiologically acceptable buffer solution.

Preferably, the ultrasonic energy is pulsed, a typical regime is 1, 2, 3, 4, 5, 6, 7 or 8 seconds on and 0.5, 1 or 2 seconds off, however it will be appreciated that the exact pulse timings is not intended to limit the scope of the invention.

Preferably, the ultrasonic power is between 100-700 Watts, and more preferably is about 400 Watts.

The ultrasonication step is preferably carried out for between 10-40 minutes, ideally for about 20 minutes and preferable is carried out at below room temperature. Ideally, ultrasonication is carried out on ice at about 4° C.

The freeze/thaw process preferably comprises freezing the tissue at, for example between −10 to −80° C., and typically at −20° C. for between 2-24 hours and subsequently defrosting the tissue for about 2, 3 or 4 hours until it reaches room temperature. This process is carried out at least once and preferably twice in the absence of a hypotonic buffer and repeated again at least once and preferably twice when the tissue is immersed in the hypotonic buffer. It will be appreciated that the freeze/thaw in the presence and absence of a hypotonic buffer may be reversed and optionally alternated. A hypotonic solution is one in which the concentration of electrolyte is below that in cells. In this situation osmotic pressure leads to the migration of water into the cells, in an attempt to equalize the electrolyte concentration inside and outside the cell walls.

Preferably, the hypotonic buffer is 10 mM Tris solution at a pH of about 8.0 and includes approximately 0.1% (w/v) EDTA and aprotinin (at a concentration of approximately 10 KIU·ml$^{-1}$).

Preferably, the incubating step with a hypotonic solution comprises a two stage hypotonic wash at incrementally elevated temperatures. The first stage is incubation for about between 12-48 hours and typically about 24 hours at below room temperature but above freezing for example at around 4° C. and the second stage incubation which for about the same period at a temperature above room temperature for example at about 37° C., a third stage (step (iv) in the embodiment where ultrasonication is performed and step (iii) when it is omitted) is performed by incubating the tissue in a hypotonic solution additionally comprising an anionic detergent.

The third wash step with the anionic detergent comprises incubation for between 1-3 days, and preferably for about 48 hours at a temperature above the second wash but below boiling for example at about 55° C.

The temperatures and periods of incubation specified above in incubation steps herein before described exemplify an appropriate protocol for the methods of the present invention and are not intended to limit the scope of the invention.

Preferably the anionic detergent is sodium dodecyl sulphate (SDS). Preferably this is present in the hypotonic wash solution at a concentration in the range of 0.03-0.3% (v/v) and more preferably still is present at approximately 0.15% (v/v).

Preferably, the three stage incubation step of steps (iii) and (iv), when ultrasonication is performed and steps (ii) and (iii) when ultrasonication is omitted are repeated for a minimum of three cycles.

Preferably, in one embodiment of the invention following step (v) when ultrasonication is performed and step (iv) when ultrasonication is omitted of the repeated hypotonic washing with and without an anionic detergent, the method further includes the step of washing the tissue in a buffer solution.

Preferably, the buffer is PBS. The wash process may comprise repeated incubations of between 1, 2 or 3 hours at a temperature of 40-60° C. and ideally at about 55° C. This step is preferably repeated a further 1, 2 or 3 times.

Preferably, the method includes an incubation (step (v) or step (vi) when an ultrasonication step is employed) with a solution comprising one or more nuclease enzymes.

The nuclease enzymes are used to digest any remaining nucleic matter which has been shown to act as sites for calcification.

A typical but non-limiting nuclease incubating solution 50 mM Tris solution pH7.5, 10 mM $MgCl_2$, bovine serum albumin (50 μg/ml) with RNase (1 U·l ml$^{-1}$) and DNase (50 U·ml$^{-1}$).

Tissue is preferably incubated for about 2, 3 or 4 hours typically at about 37° C. with the nuclease solution whilst being gently agitated.

Following incubation with the nuclease solution, the tissue is preferably then further incubated for about 12-48 hours and typically 24 hours at 30-50° C. and typically at about 37° C. in a hypertonic solution.

Preferably the hypertonic solution is Tris in solution (0.05 M) pH 7.6 plus 1.5 M NaCl and EDTA (0.1% w/v).

Preferably, the tissue is then washed in a buffer solution comprising PBS and a chelating agent for between 12-24 hours.

Preferably, the chelating agent is EDTA at a concentration of 0.1% (w/v).

Preferably, the oxidising agent of the final step of the methods of the present invention is peroxyacetic acid ($C_2H_4O_3$) also known as peracetic acid and commonly abbreviated to PAA.

Preferably, the concentration of PAA is in the range of 0.01~0.5% v/v and more preferably still is about 0.1% PAA (v/v).

Preferably, the method further includes a multi-stage incubation wash in PBS at decreasing temperatures. A typical protocol for this final stage wash is a first wash with PBS for 12-48 hours and typically 24 hours at between 35-50° C. and ideally at 45° C., a second incubation wash for a similar period at between 30-40° C. and ideally at 37° C. and a final incubation wash for a similar period at between 0-10° C. and ideally at 4° C.

Preferably, the multi-stage incubation wash is repeated a further once, twice, third, fourth, fifth, sixth, seventh or eighth times.

It will be appreciated throughout the description of the methods of the present invention that the timings, temperatures and concentrations recited are given as examples only and are not intended to limit the scope of the invention.

Preferably, the method further includes the step of preserving the prepared tissue for subsequent use.

Such a step is illustrated by, for example, cryopreservation or deep freezing.

According to a further aspect of the invention there is provided a transplantation product produced by the methods of the present invention.

According to a yet further aspect of the invention there is provided meniscal tissue obtainable by the method of the present invention for use as a transplant tissue.

According to a yet further aspect of the invention there is provided use of meniscal tissue obtainable by the method of the present invention as a transplant tissue.

Preferably, the product produced by the present invention may be characterised by the absence (100%) or substantial absence (90%) of cells in the central area of the meniscal tissue.

The method of the present invention provides a means by which meniscal tissue can be prepared that is substantially devoid of cells such as fibrochondrocytes.

Preferably, the product produced by the present invention may be characterised by a genomic DNA (gDNA) content of between 0 to 20 ng/mg, more preferably by a gDNA content of 0-10 ng/mg and more preferably still be a gDNA content of 0-5 ng/mg.

The product of the present invention is therefore practically devoid of cells such as fibrochondrocytes and has a negligible if any gDNA content and as such is a most appropriate material for subsequent transplantation.

It is believed that the methods and products of the present invention advantageously provides natural meniscal tissue that is truly biocompatible with a host with minimal risk of rejection by the host by virtue of the improved method of decellularisation.

The methods of the present invention have been successfully employed to decellularise meniscal tissue from areas problematic to decellularisation in the outer and central areas of the meniscus and especially around areas of microvascularistion and deep within the centrally located tissue.

According to a yet further aspect of the invention there is provided a kit comprising the solutions as herein before described and optionally including a set of written instructions for use thereof.

According to a yet further aspect of the invention there is provided a method of treatment of an individual requiring a meniscal transplant comprising the steps of preparing a decellularised donor meniscal tissue according to the method of the first aspect of the invention and replacing the defective or damaged meniscus with the decellularised meniscus.

BRIEF DESCRIPTION OF THE DRAWINGS

The invention will now be described by way of example only with reference to the following figures wherein:

FIG. 2 shows the DNA content and histology of the medial porcine meniscus after decellularisation using various protocols. FIG. 2A shows fresh meniscus; FIG. 2B shows the meniscus after a basic decellularisation procedure; FIG. 2C shows the meniscus after decellularisation and ultrasonication; FIG. 2D shows the meniscus after decellularisation at 55° C. and ultrasonication; FIG. 2E shows the meniscus after decellularisation at 55° C., ultrasonication and freeze thaw; FIG. 2F shows the meniscus after decellularisation at 55° C. (×2), ultrasonication and freeze thaw; FIG. 2G shows the meniscus after decellularisation at 55° C. (×3-4), ultrasonication, freeze thaw and PAA treatment.

FIG. 3A shows a range of histology from fresh porcine meniscus and FIG. 3B shows the histology from comparable areas following decellularisation according to the method of the present invention.

DETAILED DESCRIPTION

Materials and Methods

Preparation of Meniscal Tissue

Figure 1:
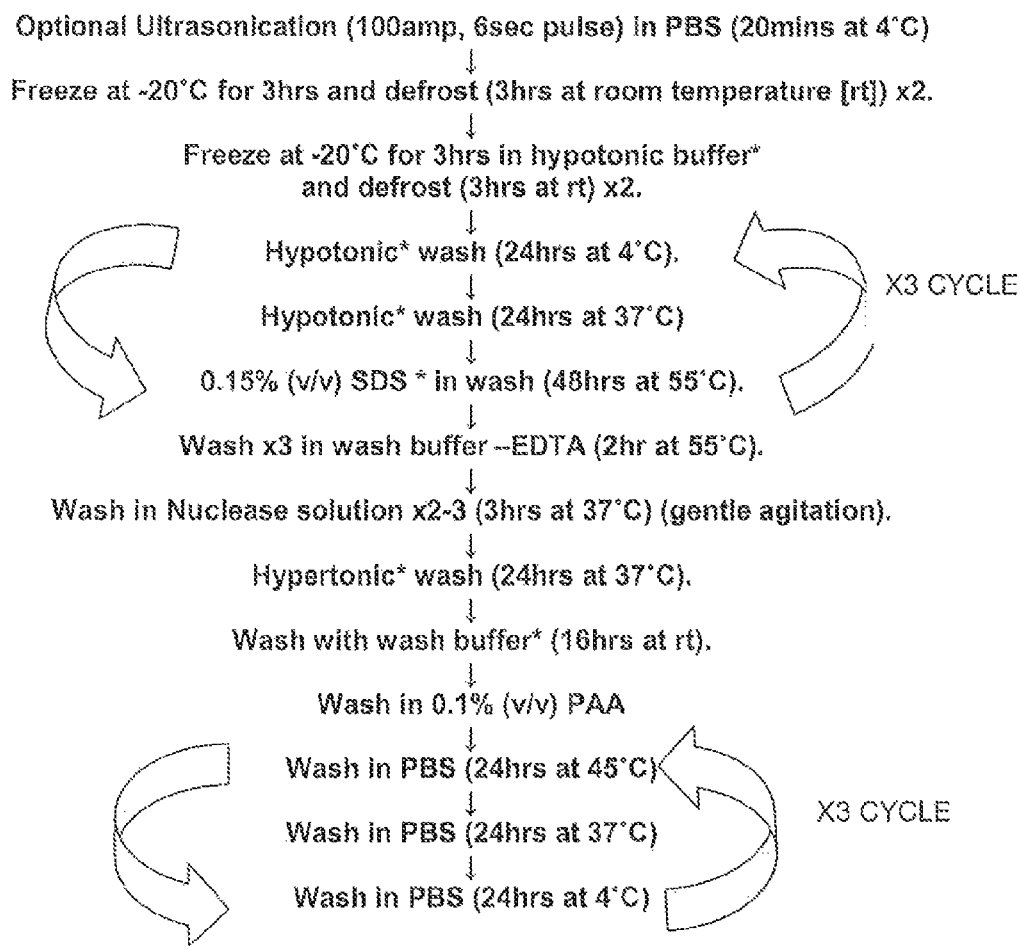
FIG. 1 shows a flow diagram of a typical step by step procedure according to the method of the present invention.

Porcine menisci were obtained from a local abattoir within 24 h of animal slaughter. The menisci were dissected from the knee joint by gently excising the knee capsule before cutting both the anterior and posterior cruciate ligaments to expose the meniscus. Incisions were then made perpendicular to the meniscal horn attachments to release the menisci. Excess tissue from the capsule and the meniscal attachments were then removed using scissors. The meniscus was then removed and washed in PBS (Oxoid) to remove excess blood. Samples were then stored at −40° C. on PBS moistened filter paper for future use.

Tissue/Histology Preparation

Tissue specimens (n=3) were fixed in 10% (v/v) neutral buffered formalin for 48 h and then dehydrated and embedded in paraffin wax. Serial sections of 6 μm in thickness were taken with 1 in 10 sections used. Standard haematoxylin and eosin (H&E) (Bios Europe Ltd, Skelmersdale, UK) staining was used to evaluate tissue histioarchitecture. Nucleic acids were stained using Hoechst dye (bis-benzimide H33258 pentahydrate; Molecular Probes, Eugene, Oreg.). Monoclonal antibodies for a-Gal obtained from Alexis biochemicals, San Diego, USA.

Ultrasonication

Tissue samples (2 cm width) were sutured to a aluminium gauze using 4-0 prolene sutures purchased from Southern Syringes Ltd. This was placed inside a 250 ml glass beaker filled with ice cold PBS kept on ice. Various ultrasonication regimens (High Intensity ultrasonication processor, 600 Watts, model 601, Progen Scientific, Mexborough, South Yorkshire) were applied to the tissue samples via positioning the tissue sample directly under the probe with the PBS being changed after every treatment. On completion, the tissue was removed and subjected to remaining decellularisation procedure. The pulse regimen was 1 second on, 1 second off for 10 mins before changing PBS and repeating.

Meniscal Indentation indentation apparatus was used to analyse the deformation under load of fresh and decellularised porcine menisci. The rig consisted of a shaft with a detachable 3 mm, cylindrical, rigid, flat indenter at one end and the other end connected to a linear variable differential transformer (LVDT) for monitoring the displacement of the shaft. Weights were placed under the LVDT and the shaft movement was initiated by a manual release mechanism. The LVDT was calibrated using step heights and the calibration factor acquired. The LVDT had a resolution of 0.001 inches. The speed of the shaft was controlled by an oil-filled dashpot. Samples (n=3) were firstly cut using a 6 mm diameter cutter to remove cylindrical shaped plugs. A section measuring 3 mm was removed from the centre of the original plugs. Samples were fixed to the base of the sample holder using double sided sticky tape (3M; Loughborough, UK) and a drop of cyanoacrylate glue. A load of approximately 2N was applied through a viscous dashpot. Samples were immersed in a PBS. Tests were run over 1 h time periods. The LVDT allowed the generation of results in the format of time against voltage. Data was acquired using Lab View 8 (National instruments, Austin, U.S.A) and on application of the calibration factor, results were converted to time against deformation (mm).

Hydroxyproline Assay.

Prior to performing the hydroxyproline assay, samples (n=3) were lyophilized to a constant weight before being hydrolysed by incubation with 6M hydrochloric acid (HCL) for 4 h at 120° C. and neutralized using sodium hydroxide (NaOH). The procedure adopted was based on the method described by Edwards and O'Brien [29]. Standard calibrator solutions were made up using trans-4-hydroxy-L-proline (Sigma). Test solution (50 µl) was added to wells of a flat bottomed 96-well plate to which 100 µl of oxidizing solution (chloramine T hydrate; Sigma) was added and left for 5 min with gentle agitation. Ehrlich's reagent (100 µl) was then added to each well. The plate was then covered and incubated at 60° C. in a water bath for 45 min prior to the absorbance being read at 570 nm. The concentration of hydroxyproline was then determined by interpolation from a hydroxyproline standard curve.

Sulphated Sugar Assay.

Prior to performing the sulphated sugar assay, samples (n=3) were lyophilized to a constant weight before enzymatically digesting the tissue in papain buffer (1 mg·ml$^{-1}$ papain, Sigma, in PBS at pH 6.0 with 5 mM cysteine-HCl, Sigma, and 5 mM Na$_2$EDTA, VWR) for 48 h at 60° C. The method was adapted from Farndale et al. [30]. Briefly, standard calibrator solutions were made up using chondroitin sulphate (Sigma). Standard or test solution (40 µl) were added to 250 µl of 1,9-dimethylene blue solution in wells of flat bottomed 96-well plates. The absorbance was then read at 525 nm after 1 min. The resultant concentration of sulphated sugars, representative of glycosaminoglycans (GAG) was then determined by interpolation from the standard curve.

Extraction and Analysis of gDNA Presence

Genomic DNA (gDNA) was extracted using a DNA isolation kit for tissues (Roche Applied Sciences, Indianapolis, USA). Briefly, 200 mg of fresh and decellularized porcine meniscal tissue was digested using a Proteinase K solution (n=3). Following this, an RNase solution was applied to digest the RNA present within the samples. A protein precipitation solution was then added and samples were centrifuged (15,000 g, 20 min at 20° C.). Isopropanol (0.7 volumes, VWR) was then added to the pellet to recover any DNA present. The isolated DNA pellet was then washed with ice-cold 70% (v/v) ethanol and left to air dry prior to resuspension in tris-EDTA buffer (Sigma).

Qualitatively the presence of gDNA was analysed using an E-gel PowerBase system (Invitrogen, Paisley, UK). A dry 2% (w/v) Agarose E-gel (Invitrogen) was inserted into the base prior to the addition of samples. Resuspended samples (4 µl) were prepared by adding loading buffer (2 µl, Invitrogen) to allow ease of sample loading. The total volume was then loaded into individual lanes of the E-gel and then electophoresed. A 1 kb DNA ladder (Fermentas Inc, Sheriff Hutton, UK) was run in parallel to estimate the size of the DNA isolated. Staining with ethidium bromide allowed visual inspection on a Kodak Gel Logic 1500 system (Eastman Kodak Company, Harrow, UK). DNA was quantitated by measuring absorbance at 260-280 nm in a Nanodrop spectrophotometer (Labtech Int, Ringmer, UK).

EXAMPLE 1

With reference to FIG. 1 there is shown a typical flow chart of one embodiment of the method of the present invention. With regard to the protocol of FIG. 1 the order of ultrasonication and freeze/thawing may be reversed, however as will be demonstrated hereinafter the steps of ultrasonication, freeze/thawing and treatment with PAA are essential in order to effect total decellularisation of meniscal tissue.

EXAMPLE 2

With reference to FIG. 2A-G, there is shown a schematic representation of the meniscus as a right-angled triangle to approximate the overall cross sectional shape of the meniscus and a Hoechst stain showing the DNA content of cells which is an indication of cell density. In addition histology slides are provided to the right. FIGS. 2A-G shows the DNA content and histology of the medial porcine meniscus after decellularisation using various protocols.

FIG. 2A shows fresh porcine medial meniscus and the presence of cells throughout the tissue with a uniform distribution of DNA content of cells or cell density from the outer to inner regions of the meniscus.

The protocol followed for decellularisation of porcine medial meniscus in FIG. 2B is described in Booth, C et al "Tissue engineering of cardiac valve prostheses I: Development and histological characterisation of an acellular porcine scaffold" *The Journal of Heart Valve Disease* 11, pp. 457-462, (2002). This process does not involve ultrasonication or freeze/thawing but it does employ an SDS incubation step at room temperature. The results for DNA content following this procedure shows that cells have been removed from the meniscus peripheral area only and that cells are still present in the inner area. The protocol employed in FIG. 2C is the protocol as described in Booth et al plus an additional ultrasonication step. The results show that although peripheral cells have been removed along with some from the inner area, cells still persist throughout most of the meniscus. Following the same protocol as that for FIG. 2C but with the decellularisation anionic detergent (SDS) at an elevated temperature (55° C.) results (FIG. 2D) show that although cells have been totally removed from a significant proportion of the meniscus they are still present in the centre of the meniscus even though at a reduced density. With regard to the protocol followed in FIG. 2E, this shows the meniscus after decellularisation at 55° C., ultrasonication and freeze/thaw. The results show that cells are found at a low density throughout the central area with a predomination of cell numbers localized around microvascularisation. In the protocol followed for FIG. 2F, decellularisation at 55° C. (×2), ultrasonication and freeze/thaw the results are even better, in so far as, there are very few cells remaining and that the cells have lysed and are randomly located within the center of the meniscus. Turning to the results of FIG. 2G which employs the method of the present invention as depicted in FIG. 1 of decellularisation at 55° C. (×3), ultrasonication, freeze/thaw and PAA treatment, there is seen a complete removal of cells. The Hoescht stain shows a total absence of DNA due to complete cell removal.

The results obtained from the various decellularisation protocols show that using the method of the present invention complete decellularisation can be achieved which is not possible with any of the incomplete protocols tested or with other prior art methods.

EXAMPLE 3

Figure 3A:
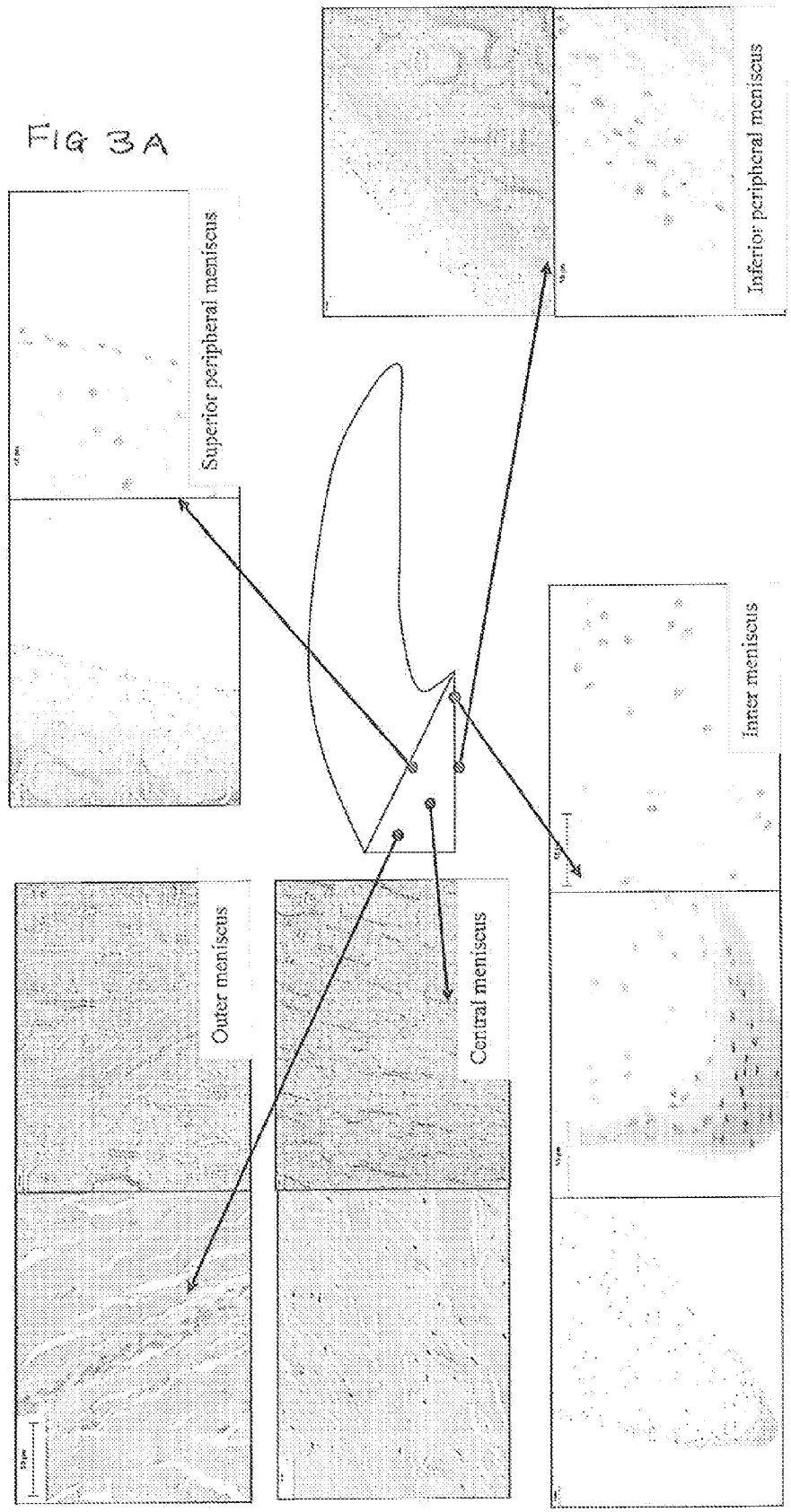

With reference to FIG. 3A there is shown cell distribution within fresh medial porcine meniscus. A cross-sectional area of the meniscus approximates to a right-angled triangle (see FIGS. 2A-G) and shows that the areas problematic to decellularisation include the outer and central areas of the meniscus, especially around microvascularisation deep within the centrally located tissue. As shown in Example 2A-E the areas which could be decellularised using an incomplete method according to the present invention were the superior and inferior peripheral meniscus and the inner meniscus. With reference to FIG. 3B there is shown a comparable section of a porcine medial meniscus decellularised according to the method of the present invention wherein the meniscus, including the problematic outer and central areas, is completely devoid of cells, in other words the meniscus is completely decellularised and provides a tissue that is suitable for transplantation into a host.

EXAMPLE 4

Figure 4:
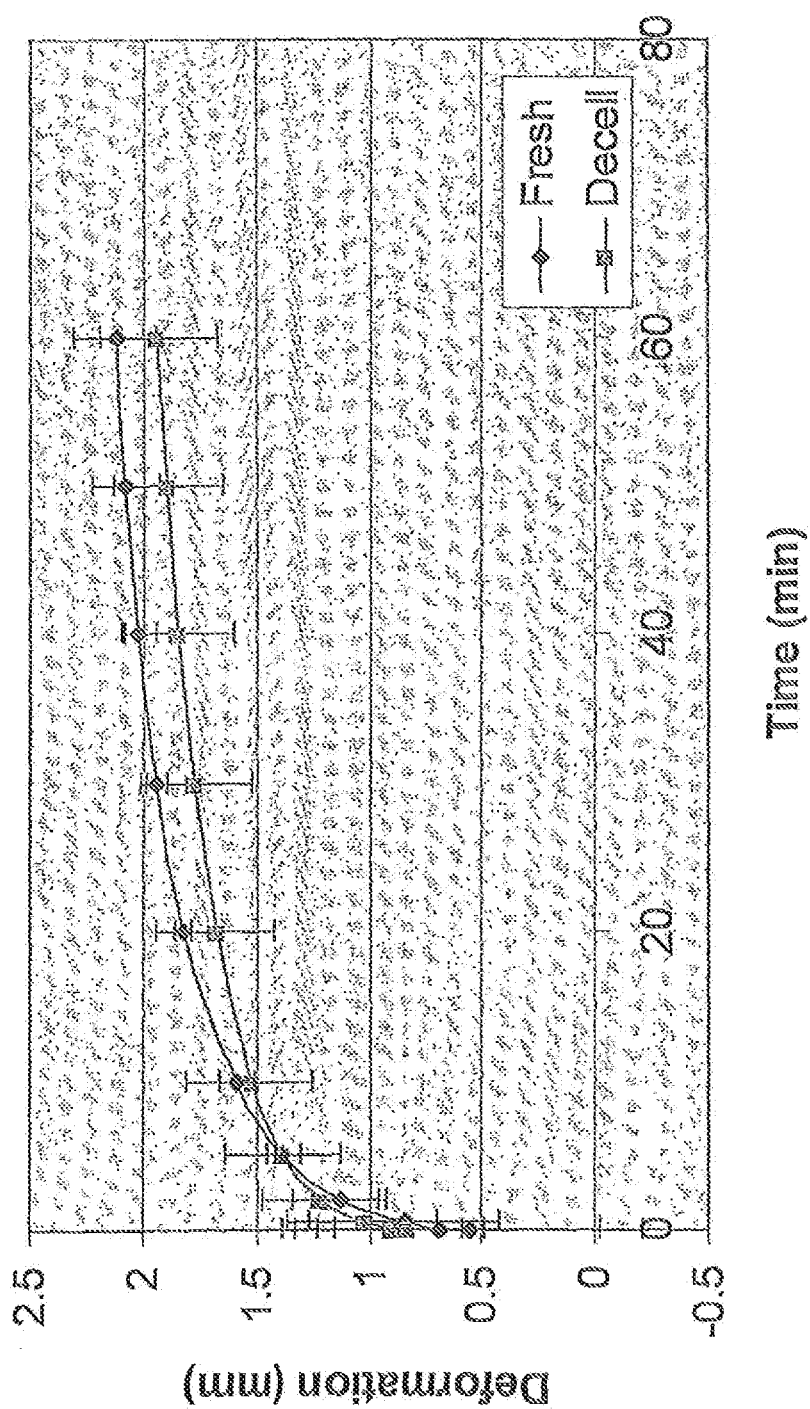
FIG. 4 shows biomechanical data for fresh and decellularised meniscal tissue.

FIG. 4 shows a graph of deformation against time for both fresh and decellularised menisci that has been decellularised according to the methods of the present invention. The data provides an illustration of a biomechanical test using indentation. The results show that decellularised meniscus has similar compressive biomechanical properties as compared to fresh tissue and therefore has commensurate physical properties and is suitable for implantation into a host.

EXAMPLE 5

Figure 5A:
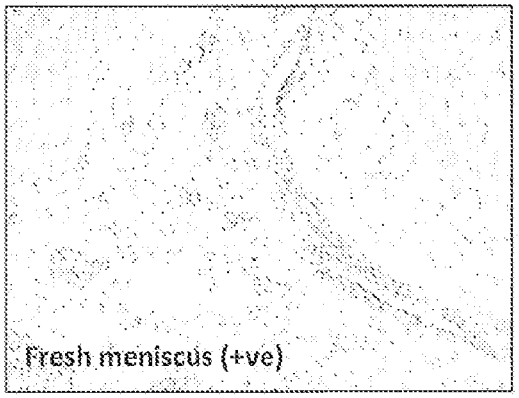
FIG. 5 shows immunoperoxidase staining for alpha-gal in fresh and decellularised meniscal tissue
Figure 5B:
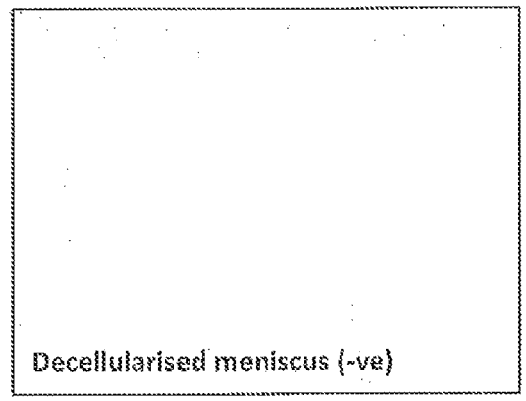

The xenogenic Gal α 1-3 Gal β 1-4 Glc NAc-R or alpha-Gal epitope is known to be responsible for hyperacute rejection in xenotransplantation. In tissue engineering residual alpha-Gal epitope may induce severe inflammation in humans and may lead to graft failure. FIG. 5A shows the positive immunoperoxidase staining for the presence of the alpha-Gal epitope using a monoclonal anti-alpha-Gal antibody in fresh porcine medial meniscus. When compared to a meniscus decellularised according to the methods of the present invention, FIG. 5B shows an absence of the epitope by way of a negative stain. These results show that the meniscus prepared by the methods of the present invention is alpha-Gal epitope deficient and thus is suitable for implantation into a human host.

EXAMPLE 6

The concentration of hydroxyproline per mg of dry weight of the fresh porcine meniscal tissue was 143.3 (±23.29) $\mu g \cdot mg^{-1}$. Following decellularization the concentration of hydroxyproline was found to be 123.96 (±36.3) $\mu g \cdot mg^{-1}$. There was no significant difference in the hydroxyproline content of the fresh tissue compared to the decellularised tissue (ANOVA, p>0.05).

EXAMPLE 7

The concentration of sulphated sugars per mg of dry weight of the fresh porcine meniscal tissue was 30.3 (±3.9) $\mu g \cdot mg^{-1}$. Following decellularization the concentration of sulphated sugars was found to be 12.3 (±1.6) $\mu g \cdot mg^{-1}$, indicating a loss of 59.4%. There was a significant difference in the sulphated sugars content of the fresh tissue when compared to the decellularized tissue (ANOVA, p<0.05), indicating loss of GAG's.

EXAMPLE 8

Decellularized meniscal tissue samples treated to extract genomic DNA (gDNA), loaded and electrophoresed on an agarose gel confirmed the absence of gDNA in comparison to the fresh meniscal tissue which displayed a clear band around 10,000 base pairs (not shown). Results were quantitatively verified using spectrophotometry, in which a peak of absorbance between 260-280 nm was seen for fresh tissue sample indicating the presence of gDNA. This peak corresponded to 40 (±9.7) $ng \cdot mg^{-1}$. A small peak was also recorded for decellularized tissue corresponding to 2 (±0.5) $ng \cdot mg^{-1}$.

In conclusion, the methods of the present invention show that it is possible to provide a completely decellularised and immunologically inert porcine or human donor meniscal tissue that retains its physical properties. Such menisci may be used for subsequent implantation into a host thus avoiding or minimising the likelihood of transplant rejection whilst providing the same strength and functional capabilities as that of a healthy meniscus.

The invention claimed is:

1. A method of preparing donor meniscal tissue for subsequent implantation into a host comprising:
   (i) thawing a frozen meniscal tissue;
   (ii) incubating the tissue in a hypotonic solution;
   (iii) incubating the tissue in a hypotonic solution comprising an anionic detergent;
   (iv) repeating (ii) and (iii);
   (v) incubating the tissue in a solution comprising at least one nuclease enzyme; and
   (vi) washing the tissue with an oxidising agent, wherein the meniscal tissue is devoid of cells in the central area of the meniscal tissue and retains its original histoarchitecture.

2. The method according to claim 1 further including ultrasonicating the tissue in a buffered solution prior to step (i).

3. The method according to claim 1, wherein step (i) further comprises repeated cycles of freezing and thawing the meniscal tissue.

4. The method according to claim 3, wherein the repeated cycles of freezing and thawing the meniscal tissue comprises freezing the tissue at a temperature in a range of between −10° C. to −80° C. for a period of time in a range of between two and 24 hours and then subsequently thawing the tissue until the tissue is defrosted.

5. The method according to claim 3, wherein freezing and thawing the tissue is carried out at least one or more times in the absence of a hypotonic buffer and repeated one or more times when the tissue is immersed in a hypotonic buffer solution.

6. The method according to claim 1, wherein the donor meniscal tissue is obtainable by removing a whole or a portion of a medial or lateral meniscus from a knee joint of an allogeneic or xenogeneic donor.

7. The method according to claim 1, wherein step (ii) comprises a two-stage hypotonic wash at incrementally elevated temperatures.

8. The method according to claim 7 wherein step (iii) comprises incubating the tissue for a period of between one and 3 days and the incubation temperature is above that of the incubation in the hypotonic solution of step (ii).

9. The method according to claim 1 further including washing the tissue in a buffer solution comprising a chelating agent after step (iv).

10. The method according to claim 1, wherein the incubation with a solution comprising one or more nuclease enzymes is subsequent to the repeated incubations.

11. The method according to claim 1 further comprising incubating the tissue in a hypertonic solution with ethylenediaminetetraacetic acid (EDTA) for a period of time in a range between 12 and 48 hours at a temperature in a range of between 30° C. and 50° C. following the incubation with a solution comprising nucleases.

12. The method according to claim 1, wherein the tissue is washed in a buffer solution comprising phosphate buffered saline (PBS) and EDTA for a period of time in a range between 12 and 24 hours following incubation in a solution comprising nucleases.

13. The method according to claim 1, wherein the oxidizing agent employed in washing the tissue with an oxidising agent is peroxyacetic acid ($C_2H_4O_3$) or peracetic acid (PAA).

14. The method according to claim 13, wherein the concentration of PAA is in the range of 0.01-0.5% v/v.

15. The method according to claim 1 further comprising a multi-stage incubation wash in PBS at decreasing temperatures following the washing of the tissue in the presence of an oxidising agent.

16. The method according to claim 1, wherein ultrasonication is performed in advance of thawing the frozen meniscal tissue or after thawing the frozen meniscal tissue.

17. A method of preparing donor meniscal tissue for subsequent implantation into a host comprising:
   (i) ultrasonicating the tissue in a buffered solution;
   (ii) repeating cycles of freezing and thawing the tissue;
   (iii) incubating the tissue in a hypotonic solution;
   (iv) incubating the tissue in a hypotonic solution comprising an anionic detergent;
   (v) repeating (iii) and (iv);
   (vi) incubating the tissue in a solution comprising at least one nuclease enzyme; and
   (vii) washing the tissue with an oxidising agent, wherein the meniscal tissue is devoid of cells in the central area of the meniscal tissue and retains its original histoarchitecture.

18. A product comprising meniscal tissue obtained by the method of claim 17, wherein the meniscal tissue is devoid of cells in the central area of the meniscal tissue and retains its original histoarchitecture.

19. A meniscal transplantation product that is devoid of cells in the central area of the meniscal tissue and retains its original histoarchitecture.

20. The meniscal product according to claim 19, wherein the meniscal product comprises a genomic DNA (gDNA) content of between 0 to 20 ng/mg.

21. The meniscal product according to claim 20, wherein the gDNA content is in a range between zero and 10 ng/mg.

22. The meniscal product according to claim 20, wherein the gDNA content is in a range between zero and 5 ng/mg.

23. A product comprising meniscal tissue obtained by the method of claim 17, wherein the meniscal tissue is up to 35 mm in thickness and has an absence or substantial absence of cells in the central area of the meniscal tissue and retains its original histoarchitecture, wherein absence of cells means the tissue is 100% free of cells and substantial absence means the tissue is at least 90% free of cells.

24. The product of claim 23, wherein a starting material is a whole meniscus.

25. A meniscal transplantation product that is up to 35 mm in thickness and has an absence or substantial absence of cells in the central area of the meniscal tissue and retains its original histoarchitecture, wherein absence of cells means the tissue is 100% free of cells and substantial absence means the tissue is at least 90% free of cells.

26. The product of claim 25, wherein a starting material is a whole meniscus.

27. A method of treatment of an individual requiring a meniscal transplant comprising replacing a defective or damaged meniscus with the product of claim 18.

* * * * *